United States Patent [19]
Koli et al.

[11] Patent Number: 5,424,074
[45] Date of Patent: Jun. 13, 1995

[54] PHARMACEUTICAL COMPOSITION FOR POTASSIUM SUPPLEMENTATION

[75] Inventors: Hideaki Koli, Itano; Hirofumi Ueno; Kyosuke Masaki, both of Kurume; Akihisa Takaichi, Naruto; Toshihiko Okamoto; Toshiaki Matsumoto, both of Tokushima, all of Japan

[73] Assignee: Otsuka Pharmaceutical Co., Ltd., Tokyo, Japan

[21] Appl. No.: 189,285

[22] Filed: Jan. 31, 1994

Related U.S. Application Data

[63] Continuation of Ser. No. 945,595, Sep. 16, 1992, abandoned, which is a continuation of Ser. No. 655,366, Feb. 19, 1991, abandoned.

[30] Foreign Application Priority Data

Jun. 20, 1989 [JP] Japan ................................ 1-157330

[51] Int. Cl.⁶ .............................................. A61K 33/00
[52] U.S. Cl. .................................... 424/464; 424/451; 424/484; 424/489; 424/466
[58] Field of Search ................ 424/440, 466, 464, 451, 424/484, 489, 682, 722

[56] References Cited

U.S. PATENT DOCUMENTS 4,867,989  9/1989  Silva ..................................... 424/440

OTHER PUBLICATIONS

Budavari et al. (1989). The Merck Index, Merck & Co., Inc.
Fein, H. D., eds., "Modern Drug Encyclopedia and Therapeutic Index", (8th ed.) p. 254. (1961).

*Primary Examiner*—Thurman K. Page
*Assistant Examiner*—Raj Bawa
*Attorney, Agent, or Firm*—Sughrue, Mion, Zinn, Macpeak & Seas

[57] ABSTRACT

This invention provides a magnesium-added potassium-supplementing pharmaceutical composition containing 3 to 15 wt. %, as K, of a potassium-containing compound and 0.2 to 5 wt. %, as Mg, of a magnesium-containing compound in a K/Mg weight ratio of 20:1 through 1:1, and particularly a magnesium-added potassium-supplementing pharmaceutical composition in an effervescent dosage form which contains the above-mentioned ingredients, in the indicated ratio, in combination with 7 to 20 percent by weight of a blowing agent and 15 to 60 percent by weight of a neutralizing agent.

20 Claims, No Drawings

# PHARMACEUTICAL COMPOSITION FOR POTASSIUM SUPPLEMENTATION

This is a Continuation of patent application Ser. No. 07/945,595, filed Sep. 16, 1992, now abandoned, which in turn is a Continuation of Grandparent application Ser. No. 07/655,366, filed on Feb. 19, 1991, now abandoned.

TECHNICAL FIELD

The present invention relates to a magnesium-added potassium-supplementing pharmaceutical composition and more particularly to a novel magnesium-added potassium-supplementing pharmaceutical composition which provides the body with potassium with high efficiency, particularly the composition in effervescent dosage forms.

BACKGROUND ART

The living body needs potassium (K) and a shortage of K results in pathologic states such as potassium deficiency. Potassium deficiency is sometimes accompanied by hypoparathyroidism (insufficiency of accessory thyroid gland), vitamin deficiency, osteomalacia, sprue, nephrosis, renal failure, etc. and it has recently been pointed out that depletion of body potassium leads to a dearrangement in Na (sodium)/K ratio and, through the resulting increased tension of the vascular wall etc., induces such disorders as hypertension.

The amount of K which an average adult requires per day is 0.4 mEq/kg (about 1,000 mg/60 kg body weight) according to "Nutritional Requirements for the Japanese" (edited by Health Promotion and Nutrition Section, Bureau of Health and Medical Care, the Ministry of Health and Welfare, 1984). This amount of K is mostly obtained from vegetables and fruits and, in consideration of its ratio to Na, the required intake has been calculated to be 2–4 g per day [Nutritional Requirements for the Japanese, 4th Revised Edition, 1989]. However, inadequacy in K intake due to biased diets and efflux and depletion of body potassium due to diarrheas associated with stress and drinking are the order of the day and when such condition persists long, one is afflicted with K deficiency and associated diseases mentioned above.

However, there has not been commercially available a K-supplementing preparation that may easily and rapidly fulfil the need for K supplementation in such K-defficiency and, associated diseases.

DISCLOSURE OF THE INVENTION

The object of the present invention is to provide a novel K-supplementing pharmaceutical composition for K defficiency and more particularly to a pharmaceutical composition which is of clinically and practically useful, superior in formulated uniformity and stability, easy to ingest (easy to take by mouth and palatable) and able to insure a stable and adequate supply of K.

To accomplish the above-mentioned object, the inventors of the present invention conducted an intensive research and, as a consequence, they discovered that a composition containing a definable amount of a K-containing compound together with a magnesium (Mg)-containing compound, both as essential ingredients, particularly in an effervescent dosage form, precludes an intracellular retention of Na on account of the action of Mg contained therein and stimulates the uptake of K into the cells to thereby reduce the Na/K ratio, thus meeting the above-mentioned object. The present invention has been developed on the basis of the above finding.

Thus, in accordance with the present invention, there is provided a novel Mg-added K-supplementing pharmaceutical composition characterized in that said composition contains 3 to 15 percent by weight, as K, of a K-containing compound and 0.2 to 5 percent by weight, as Mg, of a Mg-containing compound, in a K/Mg weight ratio of 20:1 through 1:1.

In consideration of water dispersibility, solubility and ease of ingestion, the pharmaceutical composition of the present invention is preferably provided in an effervescent dosage form containing an effervescing agent and a neutralizer. Thus, the effervescent pharmaceutical composition of the invention is characterized by containing 3 to 15 percent by weight, as K, of a K-containing compound and 0.2 to 5 percent by weight, as Mg, of a magnesium-containing compound in a K/Mg weight ratio of 20:1 through 1:1, in combination with 7 to 20 percent by weight of an effervescing agent and 15 to 60 percent by weight of a neutralizing agent.

The K-supplementing pharmaceutical composition, particularly the K-supplementing effervescent composition, of the present invention has excellent formulated stability in such dosage forms at tablets, granules, capsules, etc., particularly in the tablet form, and is high in solubility and dispersibility so that simply by putting it in water before use, the K-containing compound and Mg-containing compound contained in the composition can be easily and evenly dissolved and dispersed with evolution of carbon dioxide gas due to neutralization, giving a solution well paratable and sufficient to provide the body with adequate amounts of K and Mg. Therefore, the pharmaceutical composition of the invention is expected to be of value in the treatment and improvement of hypokalemia, K deficiency, Mg deficiency, etc. and, by encouraging the people of today in whom K and Mg tend to be depleted to take adequate amounts of K and Mg and to thereby help them obviate the risk of K and Mg deficiencies and keep themselves in good health.

The K-containing compound as an ingredient of the pharmaceutical composition of the present invention includes, inter alia, potassium carbonate, monopotassium phosphate, dipotassium phosphate, tripotassium phosphate trihydrate, potassium pyrophosphate, potassium polyphosphate, potassium chloride, potassium hydrogen L-tartarate, potassium hydrogen DL-tartarate, potassium nitrate, potassium metabisulfite, potassium sorbate, potassium citrate, potassium gluconate, potassium aspartate, potassium hydrogen carbonate, potassium acetate, potassium pyrosulfite, potassium lactate, potassium alginate, potassium glutamate and so on. Particularly preferred are potassium hydrogen carbonate and potassium carbonate. The Mg-containing compound includes, inter alia, magnesium chloride, magnesium sulfate, magnesium carbonate, magnesium oxide, magnesium citrate, magnesium acetate, magnesium gluconate, magnesium aspartate, magnesium nitrate, magnesium silicate aluminate, magnesium silicate and so on. Particularly preferred are magnesium sulfate and magnesium carbonate.

These K-containing compounds and Mg-containing compounds can be utilized with advantage in the forms commonly available, namely as powders not larger than 200 μm in size. These may be incorporated independently or in combination in the pharmaceutical composition of the invention and the proportions thereof are generally 3 to 15% (% by weight; the same applies hereinafter), preferably 4 to 10%, as K, for the K-containing compound and 0.2 to 5%, preferably 0.5 to 2%, as Mg, for the magnesium-containing compound. However, the weight ratio of K to Mg must be within the range of 20:1 through 1:1, preferably 14:1 to 3:1. Only when the K/Mg ratio is within the above range, the desired beneficial effect, particularly the promoting effect on cell uptake of K, of the invention is fully realized. Thus, even when the K-containing compound and Mg-containing compound are within the respective ranges mentioned above, the desired effect of the invention is not obtained if the K/Mg ratio deviates from the above range. Thus, if the proportion of K is less than the specified range, the effect of K supplementation will be inadequate, while an excess of K will abolish the K uptake-promoting effect of Mg.

The preferred dosage form for the pharmaceutical composition of the present invention is an effervescent preparation and such a preparation should contain not only said K- and Mg-containing compounds in the indicated ratio but also an effervescing agent and a neutralizing agent as essential ingredients. The effervescing agent to be employed in the practice of the invention is selected from the group consisting of potassium hydrogen carbonate, potassium carbonate, sodium hydrogen carbonate, sodium carbonate and magnesium carbonate and these agents can be used independently or in combination. However, when potassium hydrogen carbonate and/or potassium carbonate is used as said an effervescing agent, it is necessary to adjust for its amount in the calculation of the K content of the composition, for this effervescing agent also functions as said K-containing compound. If the necessary amount of an effervescing agent cannot be provided with potassium hydrogen carbonate and/or potassium carbonate, other effervescing agents, namely sodium hydrogen carbonate, sodium carbonate and/or magnesium carbonate may be used in conjunction. However, since magnesium carbonate functions as said Mg-containing compound as well, its proportion should also be controlled so that the total amount of Mg in the composition remains within the above-mentioned range for Mg. If the necessary amount of an effervescing agent can be provided with sodium hydrogen carbonate and/or sodium carbonate, other compounds than potassium carbonate and potassium hydrogen carbonate can be employed as said K-containing compound.

The neutralizing agent is an acid compound capable of neutralizing said effervescing agent to liberate carbon dioxide gas. The acid compound includes, inter alia, organic acids such as L-tartaric acid, citric acid, fumaric acid, ascorbic acid, gluconic acid, acetic acid, lactic acid, malic acid, glutamic acid, benzoic acid, sorbic acid, nicotinic acid, butyric acid and so The preferred proportions of said effervescing agent and neutralizing agent in the pharmaceutical composition of the present invention is such that when the effervescent preparation is dissolved in water, the resulting solution assumes acidity of the order of pH about 3.5 to 5.0, preferably pH about 3.8 to 4.5. Thus, the preferred ranges are 7 to 20% for the effervescing agent and 15 to 60% for the neutralizing agent. More particularly, the ranges for the specific effervescing agents, are 2 to 15%, preferably 3 to 10%, for sodium carbonate, 2 to 15%, preferably 3 to 10% for sodium hydrogen carbonate, 5 to 25%, preferably 6 to 20%, for potassium carbonate, 2 to 20%, preferably 1.5 to 15%, for potassium hydrogen carbonate, and not more than about 0.5% for magnesium carbonate. The neutralizing agent is preferably selected from the range of 15 to 60%, preferably 20 to 50%. It is most beneficial to employ L-tartaric acid and/or citric acid in the range of 20 to 25% and L-ascorbic acid in the range of 5 to 5%. The incorporation of said effervescing agent and neutralizing agent brings forth the beneficial effects of the present invention.

In addition to the aforesaid essential ingredients, namely said K-containing compound and Mg-containing compound, or these compounds plus said effervescing agent and neutralizing agent, the pharmaceutical composition of the present invention may contain, as required, such other additives, each in an appropriate proportion, as the excipient, binder, disintegrating agent, lubricant, thickener, surfactant, osmotic pressure regulator, electrolytes, sweetener, flavor, color, pH adjusting agent and so on. Among the additives which may thus be incorporated include, among others, various excipients, e.g. starches such as wheat starch, potato starch, corn starch, dextrin, etc., sugars such as sucrose, glucose, fructose, maltose, xylose, lactose, etc., sugar alcohols such as sorbitol, mannitol, maltitol, xylitol, etc., and sugar rearrangement glucosides such as coupling sugar, palatinose, etc., calcium phosphate, calcium sulfate, etc.; binder-thickners such as starch, sugars, gelatin, gum arabic, dextrin, methylcellulose, polyvinylpyrrolidone, polyvinyl alcohol, hydroxypropylcellulose, xanthane gum, pectin, gum tragacanth, casein, alginic acid, etc.; lubricants such as leucine, isoleucine, L-valine, sugar ester, hydrogenated oil, stearic acid, magnesium stearate, talc, macrogols, etc.; disintegrating agents such as Avicel, CMC, CMC-Na, CMC-Ca, etc.; surfactants such as polysorbate, lecithin, etc.; and sweeteners such as sugars, sugar alcohols, dipeptides, e.g. aspartame and alitame, stevia, saccharin, and so on. These additives can be used in appropriate amounts chosen in consideration of their relations with said essential ingredients, the expected characteristics of the pharmaceutical composition and the manufacturing process.

The pharmaceutical composition of the present invention may further contain suitable amounts of vitamins, particularly cyanocobalamin and ascorbic acid (Vitamin C). This vitamin C functions as an antioxidant, too. In any event, the incorporation of these vitamins is preferred for supplementation of vitamins through the pharmaceutical composition of the invention. While the proportions of vitamins are not critical, the preferred range for vitamin C, for instance, is generally up to 30%, preferably about 5 to 25%.

The pharmaceutical composition of the present invention can be manufactured by the established pharmaceutical procedures. Taking the effervescent composition as an example, it can be manufactured by the steps of weighing out the respective ingredients, blending them, and molding the blend by the direct powder compression technique or the dry or wet granulation compression technique.

The resulting pharmaceutical composition of the present invention is administered by the route pertinent to the particular dosage form and generally by the oral route. Particularly the effervescent preparation can be simply put in water to provide a potable product suitable for ingestion or oral administration.

The dosage depends on the age, sex and body weight of the recipient and the severity of disease condition but generally speaking, 1 to 2 effervescent tablets, about 1.5 to 6.0 g per tablet, are dissolved in 100 to 300 ml of water per dosing.

The pharmaceutical composition of the present invention is not limited to the above-mentioned tablet form but, provided that the compositional range defined hereinbefore is adhered to, it may be provided in such other dosage forms as granules, powders, capsules, etc. or even in liquid forms such as an aqueous solution. The effervescent pharmaceutical composition of the invention can also be provided in appropriate dosage forms which can be extemporaneously dissolved or dispersed in water for oral administration and not being limited to dosage forms for dissolution or dispersion in water, even in liquid dosage forms.

The present invention provides a novel pharmaceutical composition for K supplementation. Particularly the effervescent preparation provided by the invention is advantageous in that it is stable with a long shelf-life, ready to dissolve, and easy to ingest. The pharmaceutical composition on ingestion supplies an adequate amount of K safely to the body to display a therapeutic or improving effect in K deficiency and associated diseases and, as an additional feature, is low in energy value. Furthermore, the pharmaceutical composition of the present invention generally has a refreshing and mild taste, with the bitter taste of K well masked.

EXAMPLE

The following examples are further illustrative of the present invention. It should be understood that, in these examples, all parts and % are by weight unless otherwise indicated.

Example 1

The following ingredients were blended in the indicated proportions and the mixture was compressed into tables by the direct powder compression method to provide an effervescent pharmaceutical composition of the invention ($K^+$ 5 mEq, $Mg^+$ 2.5 mEq and $Na^+$ 4.7 mEq, 4592.3 mg per tablet, K content 4.2%, Mg content 0.7%, K/Mg ratio 6.00).

| | |
|---|---|
| Purified sucrose | 32.7% |
| L-Ascorbic acid | 21.8% |
| Citric anhydride | 22.3% |
| Aspartame | 0.9% |
| Potassium carbonate | 7.5% |
| Sodium hydrogen carbonate | 8.6% |
| Flavor | 2.0% |
| Magnesium carbonate | 0.5% |
| Magnesium sulfate trihydrate | 3.8% |

Examples 2–9

Using the ingredients indicated below in Table 1, effervescent pharmaceutical compositions of the invention were manufactured under otherwise the same conditions as in Example 1. The effervescent pharmaceutical composition of Example 1 also appear in the same Table.

TABLE 1

| Ingredient (%) | Example 1 | 2 | 3 | 4 | 5 | 6 | 7 | 8 | 9 |
|---|---|---|---|---|---|---|---|---|---|
| Purified sucrose | 32.7 | 35.5 | 31.2 | 33.8 | 30.5 | 31.7 | 29.2 | 30.4 | 25.4 |
| L-Ascorbic acid | 21.8 | 23.7 | 20.8 | 22.5 | 20.3 | 21.2 | 19.5 | 20.3 | 17.0 |
| Citric anhydride | 22.3 | 24.3 | 23.1 | 23.1 | 24.4 | 21.7 | 23.4 | 20.8 | 23.5 |
| Aspartame | 0.9 | 1.0 | 0.9 | 0.9 | 0.8 | 0.9 | 0.8 | 0.8 | 0.7 |
| Potassium carbonate | 7.5 | 7.1 | 7.2 | 6.7 | 14.8 | 6.2 | 14.1 | 5.9 | 17.6 |
| Potassium hydrogen carbonate | 0 | 1.6 | 0 | 1.6 | 0 | 12.2 | 0 | 11.7 | 0 |
| Sodium hydrogen carbonate | 8.6 | 0 | 8.3 | 0 | 3.3 | 0 | 3.2 | 0 | 0 |
| Flavor | 2.0 | 2.1 | 2.0 | 2.0 | 1.8 | 1.9 | 1.8 | 1.8 | 1.5 |
| Magnesium carbonate | 0.5 | 0.5 | 0.5 | 0.5 | 0.5 | 0.5 | 0.5 | 0.5 | 0.5 |
| Magnesium sulfate trihydrate | 3.8 | 4.2 | 8.1 | 8.8 | 3.5 | 3.6 | 7.5 | 7.8 | 13.8 |
| $K^+$ (mEq) | 5.0 | 5.0 | 5.0 | 5.0 | 10.0 | 10.0 | 10.0 | 10.0 | 15.0 |
| $Mg^+$ (mEq) | 2.5 | 2.5 | 5.0 | 5.0 | 2.5 | 2.5 | 5.0 | 5.0 | 10.0 |
| $Na^+$ (mEq) | 4.7 | 0 | 4.7 | 0 | 1.9 | 0 | 2.0 | 0 | 0 |
| Weight per tablet (mg) | 4592.3 | 4220.9 | 4812.2 | 4438.8 | 4916.9 | 4720.3 | 5135.0 | 4938.1 | 5899.5 |
| K content (%) | 4.2 | 4.6 | 4.0 | 4.4 | 8.4 | 8.4 | 8.0 | 8.0 | 10.0 |
| Mg content (%) | 0.7 | 0.7 | 1.3 | 1.4 | 0.6 | 0.6 | 1.2 | 1.2 | 2.1 |
| K/Mg ratio | 6.00 | 6.57 | 3.08 | 3.14 | 14.00 | 14.00 | 6.67 | 6.67 | 4.76 |

Examples 10–19

Using the ingredients indicated below in Table 2, K-supplementing compositions of the invention (ca. 2.1 g per tablet) were manufactured under otherwise the same conditions as in the foregoing examples.

TABLE 2

| Ingredient (%) | Example 10 | 11 | 12 | 13 | 14 | 15 | 16 | 17 | 18 | 19 |
|---|---|---|---|---|---|---|---|---|---|---|
| Potassium chloride | 0.37 | — | — | 0.37 | — | — | 0.74 | — | 1.50 | — |
| Potassium tartarate | — | 1.13 | — | — | — | 1.13 | — | — | — | — |
| Potassium citrate | — | — | 1.53 | — | 1.53 | — | — | 0.77 | — | 0.31 |
| magnesium chloride | 0.24 | — | 0.24 | — | — | — | — | — | — | — |
| Magnesium sulfate | — | 0.30 | — | — | 0.15 | 0.6 | 0.15 | — | 0.2 | — |
| Magnesium citrate | — | — | — | 0.56 | — | — | — | 0.23 | — | 0.45 |
| Purified sucrose | 1.0 | 0.67 | 0.33 | 0.6 | 0.1 | 0.2 | 1.0 | 0.7 | 0.3 | 0.5 |
| Corn starch | — | — | — | 0.5 | — | 0.1 | 0.2 | 0.2 | — | 0.35 |

TABLE 2-continued

| Ingredient (%) | Example | | | | | | | | | |
|---|---|---|---|---|---|---|---|---|---|---|
| | 10 | 11 | 12 | 13 | 14 | 15 | 16 | 17 | 18 | 19 |
| Talc | 0.5 | — | — | — | 0.3 | 0.1 | — | 0.2 | 0.1 | 0.5 |

Test Example 1

Male Sprague-Dawley rats (body weights 190–220 g) were divided into 5 groups of 7 and fed about 15 g/day of the low-K/Mg ration indicated in Table 3 for 2 weeks to establish K/Mg deficiency in the animals. Then, the compositions indicated in Table 4 (Compositions 1 to 4, for Control Group 1, Invention Group 1, Invention Group 2 and Control Group 2, respectively) were administered once. After 24 hours, rats in the respective groups were sacrificed and autopsied and the serum and tissue levels of K, Mg and Na were determined. The animals had free access to drinking water, i.e. distilled water. There also was provided a Negative Control Group which received none of the above-mentioned compositions.

TABLE 3

| Low-K/Mg ration [weight per 100 g, (equivalent)] | |
|---|---|
| K | 9 mg (0.2 mEq) |
| Mg | 4 mg (0.4 mEq) |
| Na | 460 mg (20.0 mEq) |
| Ca | 514 mg (25.6 mEq) |
| Basal diet (%) (total 100%) | |
| β-Corn starch | 38 |
| milk casein | 25 |
| α-Potato starch | 10 |
| Cellulose powder | 8 |
| Soybean oil | 6 |
| Mineral mixture | 6 |
| Purified sucrose | 5 |
| Vitamin mixture* | 2 |
| Vitamin mixture* (in 100 g) | |
| Vitamin A acetate | 50,000 IU |
| Vitamin D$_3$ | 10,000 IU |
| Vitamin E acetate | 500 mg |
| Vitamin K$_3$ | 520 mg |
| Vitamin B$_1$ hydrochloride | 120 mg |
| Vitamin B$_2$ | 400 mg |
| Vitamin B$_6$ hydrochloride | 80 mg |
| Vitamin B$_{12}$ | 0.05 mg |
| Vitamin C | 3,000 mg |
| D-Biotin | 2 mg |
| Folic acid | 20 mg |
| Calcium pantothenate | 500 mg |
| p-Aminobenzoic acid | 500 mg |
| Nicotinic acid | 600 mg |
| Inositol | 600 mg |
| Choline chloride | 20,000 mg |
| Cellulose powder | Balance |

TABLE 4

| Composition | K (mEq) | Mg (mEq) |
|---|---|---|
| Composition 1 (Control Group 1) | 1.80 | — |
| Composition 2 (Invention Group 1) | 1.80 | 0.45 |
| Composition 3 (Invention Group 2) | 1.80 | 0.90 |
| Composition 4 (Control Group 2) | — | 0.90 |

The above compositions were prepared by using tripotassium citrate monohydrate for K and magnesium sulfate for Mg and dissolving them in amounts giving the indicated equivalents in 2 ml of distilled water.

The measured levels (μEq/gww) of K, Na and Mg in soleus muscle and the Na/K ratios calculated from the data are shown in Table 5.

It should be understood that the tabulated measured values are mean values ±SD for the respective groups (n=7) and that the marks *,  and * indicate levels of significance, p<0.05, p<0.01 and p<0.001, respectively.

TABLE 5

| Group | K content | Mg content | Na content | Na/K |
|---|---|---|---|---|
| Negative Control Group | 64.3 ± 7.2 | 19.0 ± 1.2 | 61.2 ± 2.9 | 0.9619 ± 0.1094 |
| Control Group 1 | 75.4 ± 2.9** | 19.2 ± 0.8 | 56.3 ± 6.1 | 0.7491 ± 0.0971** |
| Invention Group 1 | 79.6 ± 7.8*** | 20.1 ± 1.4 | 54.5 ± 4.2 | 0.6907 ± 0.0969*** |
| Invention Group 2 | 80.6 ± 6.3*** | 20.1 ± 1.2 | 54.6 ± 6.8 | 0.6870 ± 0.1433*** |
| Control Group 2 | 66.2 ± 4.9 | 20.7 ± 1.3 | 64.3 ± 4.9 | 0.9790 ± 0.1383 |

It will be apparent from Table 5 that the pharmaceutical compositions of the present invention containing a supplemental amount of Mg in addition to K (Invention Groups 1 and 2) inhibits the tissue uptake of Na to lower the Na/K ratio in the tissue. This is probably because added Mg induces a rapid influx of K into the cells and promotes excretion of Na from the body. In any event, it is at least clear that the pharmaceutical composition of the invention is effective in the supply of K into tissues, depression of intracellular Na levels and improvement in Na/K ratio.

Referring to the above data on K, Na and Mg levels in soleus muscle, measurement of the corresponding levels in other tissues (gastrocnemial muscle, heart muscle, kidney and tibia) and serum also gave comparable results.

Thus, the pharmaceutical compositions manufactured in the above examples are useful as K/Mg-supplemented foods or drugs which are not only palatable (giving a refreshing sensation, for instance) but are effective in that K and Mg may be expediently supplemented. Particularly the effervescent compositions according to Examples 1–9 of the invention are excellent in that it is more stable, because of its being supplied in dry state, and more desirable in taste and nourishing effect than the prior art aqueous solutions. Furthermore, these compositions are ready to dissolve in water and the resulting solutions are clear and homogenous, without unsightly coloration due to pH change. Moreover, the solutions can be tinted any attractive shade as desired by adding a colorant before ingestion. In addition, the pharmaceutical composition of the invention is lightweight, stable and convenient to transport, thus being advantageous in terms of marketing and distribution. Furthermore, the composition of the invention according to Example 1 is particularly palatable, with the objectionable taste of K being fully masked, thus giving a refreshing and mild taste.

We claim:

1. A potassium and magnesium containing pharmaceutical composition, wherein said pharmaceutical composition consists essentially of:
   (A) 3 to 15 percent by weight, as potassium, of a potassium-containing compound;
   (B) 0.2 to 5 percent by weight, as magnesium, of a magnesium-containing compound; and
   (C) not more than 20 percent by weight of a sodium-containing compound,
   wherein the weight ratio of potassium to magnesium in said pharmaceutical composition is 20:1 to 1:1, and the weight ratio of sodium to potassium in said pharmaceutical composition is less than 2.9:1.

2. A potassium and magnesium containing pharmaceutical composition in an effervescent dosage form, wherein said pharmaceutical composition consists essentially of:
   (A) 3 to 15 percent by weight, as potassium, of a potassium-containing compound;
   (B) 0.2 to 5 percent by weight, as magnesium, of a magnesium-containing compound;
   (C) 7 to 20 percent by weight of an effervescing sodium-containing agent; and
   (D) 15 to 60 percent by weight of a neutralizing agent,
   wherein the weight ratio of potassium to magnesium in said pharmaceutical composition is 20:1 to 1:1, and the weight ratio of sodium to potassium in said pharmaceutical composition is less than 2.9:1.

3. A pharmaceutical composition according to claim 2 wherein said potassium-containing compound is potassium hydrogen carbonate and/or potassium carbonate.

4. A pharmaceutical composition according to claim 2 wherein said magnesium-containing compound is magnesium sulfate and/or magnesium carbonate.

5. A pharmaceutical composition according to claim 2 wherein said potassium-containing compound is contained in a proportion of 4 to 10 percent by weight.

6. A pharmaceutical composition according to claim 2 wherein said magnesium-containing compound is contained in a proportion of 0.5 to 2 percent by weight.

7. A pharmaceutical composition according to claim 2 wherein the weight ratio of potassium to magnesium is 14:1 through 3:1.

8. A pharmaceutical composition according to claim 2 wherein 20 to 25 percent by weight of L-tartaric acid and/or citric acid and 5 to 25 percent by weight of L-ascorbic acid are used as said neutralizing agent.

9. A pharmaceutical composition according to claim 1 or 2, which is in a tablet, granule, powder or capsule form.

10. A method for improving the imbalance of the sodium/potassium ratio in a patient which comprises administering a therapeutically effective amount of a pharmaceutical composition to a patient, wherein said pharmaceutical composition consists essentially of:
    (A) 3 to 15 percent by weight, as potassium, of a potassium-containing compound;
    (B) 0.2 to 5 percent by weight, as magnesium, of a magnesium-containing compound; and
    (C) not more than 20 percent by weight of a sodium-containing compound,
    wherein the weight ratio of potassium to magnesium in said pharmaceutical composition is 20:1 to 1:1, and the weight ratio of sodium to potassium in said pharmaceutical composition is less than 2.9:1.

11. A method for treating diseases associated with potassium deficiency which comprises administering a therapeutically effective amount of a pharmaceutical composition to a patient, wherein said pharmaceutical composition consists essentially of:
    (A) 3 to 15 percent by weight, as potassium, of a potassium-containing compound;
    (B) 0.2 to 5 percent by weight, as magnesium, of a magnesium-containing compound; and
    (C) not more than 20 percent by weight of a sodium-containing compound,
    wherein the weight ratio of potassium to magnesium in said pharmaceutical composition is 20:1 to 1:1, and the weight ratio of sodium to potassium in said pharmaceutical composition is less than 2.9:1.

12. The method for treating diseases associated with potassium deficiency according to claim 11, wherein said diseases are selected from the group consisting of hypoparathyroidism, vitamin deficiency, osteomalacia, sprue, nephrosis, renal failure, and hypertension.

13. The method for improving the imbalance in the sodium/potassium ratio in a patient according to claim 10, wherein said pharmaceutical composition is administered to the patient in an amount of from about 1.5 grams to about 12 grams of said pharmaceutical composition per day, and wherein said pharmaceutical composition is dissolved in 100 to 300 milliliters of water per dose.

14. A method for improving the imbalance of the sodium/potassium ratio in a patient which comprises administering a therapeutically effective amount of a pharmaceutical composition to a patient, wherein said pharmaceutical composition consists essentially of:
    (A) 3 to 15 percent by weight, as potassium, of a potassium-containing compound;
    (B) 0.2 to 5 percent by weight, as magnesium, of a magnesium-containing compound;
    (C) 7 to 20 percent by weight of an effervescing sodium-containing agent; and
    (D) 15 to 60 percent by weight of a neutralizing agent,
    wherein the weight ratio of potassium to magnesium to said pharmaceutical composition is 20:1 to 1:1, and the weight ratio of sodium to potassium in said pharmaceutical composition is less than 2.9:1.

15. A method for treating diseases associated with potassium deficiency which comprises administering a therapeutically effective amount of a pharmaceutical composition to a patient, wherein said pharmaceutical composition consists essentially of:
    (A) 3 to 15 percent by weight, as potassium, of a potassium-containing compound;
    (B) 0.2 to 5 percent by weight, as magnesium, of a magnesium-containing compound;
    (C) 7 to 20 percent by weight of an effervescing sodium-containing agent; and
    (D) 15 to 60 percent by weight of a neutralizing agent,
    wherein the weight ratio of potassium to magnesium to said pharmaceutical composition is 20:1 to 1:1, and the weight ratio of sodium to potassium in said pharmaceutical composition is less than 2.9:1.

16. The method for treating diseases associated with potassium deficiency according to claim 15, wherein said diseases are selected from the group consisting of hypoparathyroidism, vitamin deficiency, osteomalacia, sprue, nephrosis, renal failure, and hypertension.

17. The method for improving the imbalance in the sodium/potassium ratio in a patient according to claim 14, wherein said pharmaceutical composition is administered to the patient in an amount of from about 1.5 grams to about 12 grams of said pharmaceutical composition per day, and wherein said pharmaceutical composition is dissolved in 100 to 300 milliliters of water per dose.

18. A method for improving the imbalance of the sodium/potassium ratio in a patient according to claim 14, wherein said pharmaceutical composition is in a form selected from the group consisting of a tablet, granules, a powder, and capsule form.

19. The method for treating diseases associated with potassium deficiency according to claim 15, wherein said pharmaceutical composition is administered to the patient in an amount of from about 1.5 grams to about 12 grams of said pharmaceutical composition per day, and wherein said pharmaceutical composition is dissolved in 100 to 300 milliliters of water per dose.

20. A method for treating diseases associated with potassium deficiency according to claim 15, wherein said pharmaceutical composition is in a form selected from the group consisting of a tablet, granules, a powder, and capsule form.

* * * * *